(12) United States Patent
Baskerville et al.

(10) Patent No.: US 12,708,722 B2
(45) Date of Patent: Aug. 18, 2026

(54) DRUG DELIVERY DEVICE CONFIGURED FOR PAIN REDUCTION DURING INJECTION

(71) Applicant: Eli Lilly and Company, Indianapolis, IN (US)

(72) Inventors: Paul Dennis Baskerville, Greenwood, IN (US); Hemant Thakorbhai Patel, Indianapolis, IN (US); Louis Stevens Somlai, Zionsville, IN (US); Adam Nathaniel Wiesler, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 847 days.

(21) Appl. No.: 17/998,082

(22) PCT Filed: May 12, 2021

(86) PCT No.: PCT/US2021/031935
§ 371 (c)(1),
(2) Date: Nov. 7, 2022

(87) PCT Pub. No.: WO2021/236387
PCT Pub. Date: Nov. 25, 2021

(65) Prior Publication Data

US 2023/0173196 A1 Jun. 8, 2023

Related U.S. Application Data

(60) Provisional application No. 63/028,207, filed on May 21, 2020.

(51) Int. Cl.

| | |
|---|---|
| ***A61M 5/20*** | (2006.01) |
| ***A61M 5/42*** | (2006.01) |
| ***A61M 5/44*** | (2006.01) |

(52) U.S. Cl.
CPC .............. *A61M 5/422* (2013.01); *A61M 5/20* (2013.01); *A61M 5/44* (2013.01); *A61M 2205/3368* (2013.01); *A61M 2205/3613* (2013.01)

(58) Field of Classification Search
CPC ............ A61M 5/422; A61M 2005/206; A61M 2005/208; A61B 18/02
See application file for complete search history.

(56) References Cited

U.S. PATENT DOCUMENTS

| | | | |
|---|---|---|---|
| 3,563,239 | A | 2/1971 | Hill |
| 5,236,419 | A | 8/1993 | Seney |

(Continued)

FOREIGN PATENT DOCUMENTS

| | | | |
|---|---|---|---|
| CN | 207532622 | U | 6/2018 |
| JP | 2005080832 | | 3/2005 |

(Continued)

OTHER PUBLICATIONS

Machine Translation of JP 2013540545A (Year: 2013).*

(Continued)

*Primary Examiner* — Laura A Bouchelle
(74) *Attorney, Agent, or Firm* — M. Daniel Spillman

(57) ABSTRACT

An injection device may include a housing and a baseplate coupled to the housing. The baseplate may include a flange portion and an axial portion that extends from the flange portion in a longitudinal direction of the housing. The baseplate may be an opaque, polymer material that is more thermally conductive than a material of the housing. The injection device may additionally include a syringe at least partially disposed within the housing. The syringe may include a needle. The injection device may include a deployment mechanism configured to move the syringe relative to the housing from a retracted position to a deployed position (Continued)

in which the needle projects beyond the baseplate. At least a portion of the syringe may be visible when the syringe is in the retracted position.

18 Claims, 13 Drawing Sheets

(56) References Cited

U.S. PATENT DOCUMENTS

| | | | | |
|---|---|---|---|---|
| 5,578,014 | A | 11/1996 | Erez et al. | |
| 5,609,577 | A * | 3/1997 | Haber | A61M 5/3243 604/110 |
| 6,936,028 | B2 * | 8/2005 | Hommann | A61F 7/10 604/113 |
| 7,842,007 | B2 | 11/2010 | Clawson et al. | |
| 7,981,080 | B2 | 7/2011 | Halaka | |
| 8,758,419 | B1 | 6/2014 | Quisenberry et al. | |
| 9,402,957 | B2 | 8/2016 | Adams et al. | |
| 2003/0171715 | A1 | 9/2003 | Hommann et al. | |
| 2010/0049126 | A1 | 2/2010 | Bronfeld et al. | |
| 2010/0174237 | A1 | 7/2010 | Halaka | |
| 2012/0130340 | A1 | 5/2012 | Knutson | |
| 2015/0246181 | A1 * | 9/2015 | Fourt | A61M 5/31566 604/196 |
| 2016/0008540 | A1 | 1/2016 | Fourt et al. | |
| 2016/0030685 | A1 | 2/2016 | Lane | |

FOREIGN PATENT DOCUMENTS

| | | | | |
|---|---|---|---|---|
| JP | 2013540545 | A * | 11/2013 | A61N 1/37235 |
| KR | 20180020862 | A | 2/2018 | |
| NL | 1042708 | B1 | 7/2019 | |
| WO | 2018065821 | | 4/2018 | |
| WO | 2018170176 | | 9/2018 | |
| WO | 2018231868 | | 12/2018 | |
| WO | 2019183679 | | 10/2019 | |

OTHER PUBLICATIONS

Patent Cooperation Treaty International Search Report pertaining to International Application No. PCT/US2021/031935, International Filing Date: May 12, 2021; Date of Mailing: Aug. 21, 2021.

Patent Cooperation Treaty Written Opinion of the International Searching Authority pertaining to International Application No. PCT/US2021/031935, International Filing Date: May 12, 2021; Date of Mailing: Aug. 21, 2021.

* cited by examiner 101
1362
1300
1306
1324
1302

1350C
1350C
1350D
1322
1330
1325
1304
1312
1314
1350B
1302
1350A
1350A

DRUG DELIVERY DEVICE CONFIGURED FOR PAIN REDUCTION DURING INJECTION

FIELD

Disclosed embodiments are related to pharmaceutical injection devices and related methods.

BACKGROUND

Patients suffering from a number of different diseases often inject themselves with pharmaceuticals. A variety of devices have been proposed to facilitate these injections. One type of device is an automatic injection device, or autoinjector. This type of device typically includes a trigger assembly that, when operated by a user, causes the device to automatically insert into the user a needle of a syringe. After insertion of the needle, the device may automatically inject a dose of medication through the needle into the user.

SUMMARY

In some embodiments, an injection device includes a housing and a baseplate coupled to the housing. The baseplate includes a flange portion and an axial portion that extends from the flange portion in a longitudinal direction of the housing. The baseplate is an opaque, polymer material that is more thermally conductive than a material of the housing. The injection device additionally includes a syringe at least partially disposed within the housing. The syringe includes a needle. The injection device additionally includes a deployment mechanism configured to move the syringe relative to the housing from a first retracted position to a second deployed position in which the needle projects beyond the baseplate. At least a portion of the syringe is visible when the syringe is in the retracted position.

In some embodiments, a method of transferring heat to a syringe includes bringing a baseplate of an injection device into contact with a user's skin, transferring heat from the user's skin to the baseplate, and transferring heat from the baseplate to a syringe proximate the baseplate.

In some embodiments, an injection device includes a housing and a thermally conductive baseplate coupled to the housing. The baseplate includes a flange portion and an axial portion that extends from the flange portion in a longitudinal direction of the housing. The axial portion includes an opening passing through the axial portion in a direction perpendicular to the longitudinal direction. The injection device additionally includes a deployment mechanism configured to move a syringe relative to the housing from a first retracted position to a second deployed position in which a needle of the syringe projects beyond the baseplate.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

DETAILED DESCRIPTION

Figure 1:
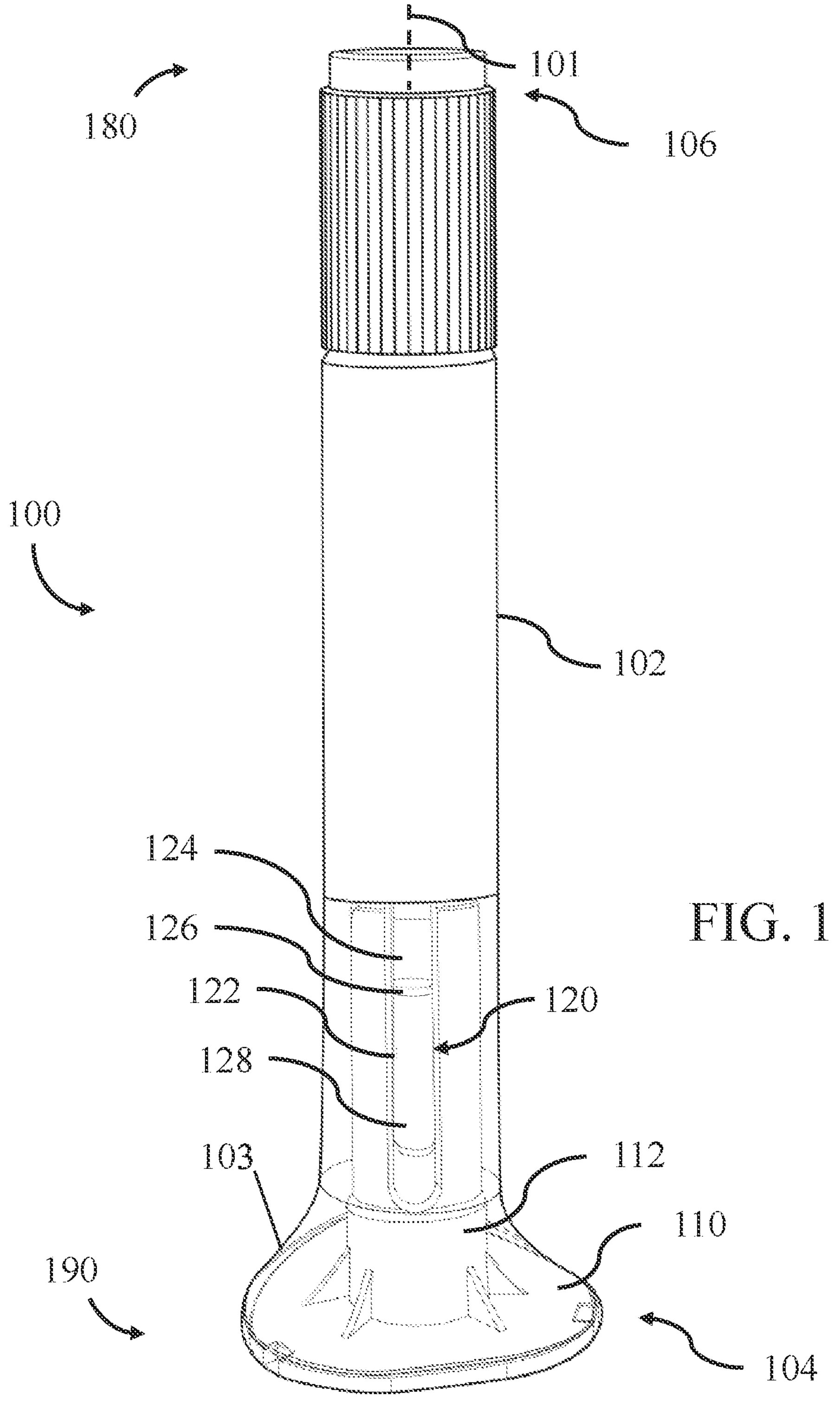
FIG. 1 is a perspective view of one embodiment of an injection device.

Autoinjectors, and other drug delivery devices, may cause pain or discomfort for a user during injection. Specifically, puncturing the skin of a user with a needle of an autoinjector may cause pain or discomfort for the user. Injecting a liquid medication after the needle is inserted may be painful or uncomfortable, especially if the liquid is cold.

The inventors have appreciated that it may be desirable to reduce pain associated with use of an injection device (or other drug delivery device), during both a needle insertion phase and a drug delivery phase, as well as potentially other phases. Accordingly, an injection device may include one or more components configured to draw heat away from a user's skin and transfer heat to medication within the injection device.

The inventors have recognized that drawing heat away from user's skin may be desirable in that it may cause a cooling effect on the user's skin. Such a cooling effect may decrease the user's perception of pain. Without wishing to be bound by theory, a cooling effect on a user's skin may serve as a distraction from any pain and/or discomfort associated with needle insertion. Additionally, a cooling effect on a user's skin may be associated with a numbing effect, which may additionally reduce pain and/or discomfort.

Transferring heat to medication within an injection device may be desirable because a user may experience less pain and/or discomfort from injection of a warmer medication compared to injection of a colder medication. Often, medication may be stored in a refrigerator (or other temperature controlled environment) prior to use, for example to promote drug stability. In such situations, the medication may be cold. Injection of cold medication may be associated with particular discomfort for a user. Warming the medication prior to injection may reduce the pain and/or discomfort experienced by the user.

In view of the considerations discussed above, it may be desirable for an injection device to include components configured to transfer heat from a user's skin to medication in the injection device.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

By way of illustration, the medication delivery device is described in the form of an autoinjector. However, the medication delivery device may be any device which is used to set and to deliver a dose of a medication, such as pen injectors, infusion pumps and syringes. The medication may be any of a type that may be delivered by such a medication delivery device. The device may be configured for a single fixed dose injection or a series of fixed dosage injections. Other embodiments of devices could be configured for a series of variable doses. The device may include a disposable device after the exhaustion of the medication or a reusable device capable of receiving a new cartridge of medication after exhaustion of the used cartridge of medication.

FIG. 1 shows an injection device in an illustrative embodiment that incorporates aspects of the invention. An injection device 100 includes a housing 102 disposed along a longitudinal axis 101, a baseplate 104 coupled to the housing 102 and disposed with a lower body portion 103 of housing 102, and an actuation mechanism 106. The baseplate 104 includes a flange portion 110 and an axial portion 112 extending from the flange portion 110.

In some embodiments, an injection device may include a proximal portion 180 and a distal portion 190. A proximal portion 180 of an injection device may include a button or activation mechanism. A distal portion 190 of an injection device may be associated with a needle or other injection device, and may contact the skin of a user proximate an injection site. The needle may be a cannula constructed of a metal or a polymer.

In some embodiments, a syringe may be disposed within an injection device. Referring to FIG. 1, a syringe 122 may include a plunger 124 with a plunger head 126, and a needle which may be obscured from view behind the baseplate 104. In some embodiments, the syringe 122 may hold a medication 128 to be injected into a user. In some embodiments, a syringe may be visible through one or more slits, windows, apertures, or other openings in the baseplate, as described in greater detail below. In the embodiment of FIG. 1, the baseplate 104 includes a slit 120 in the axial portion 112 that enables viewing of the syringe 122.

Devices described herein, such as injection device 100, 700, 900, 1300, or other kinds of injector device that may incorporate the elements of this disclosure, may further comprise medication 128, such as for example, within a reservoir provided by the syringe. In another embodiment, a system may comprise one or more devices including device and a medication. The term "medication" refers to one or more therapeutic agents including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, oxyntomodulin analogs, oxyntomodulin derivatives, therapeutic antibodies and any therapeutic agent that is capable of delivery by the above device. The medication as used in the device may be formulated with one or more excipients. The device is operated in a manner generally as described above by a patient, caregiver or healthcare professional to deliver medication to a person.

Figure 2:
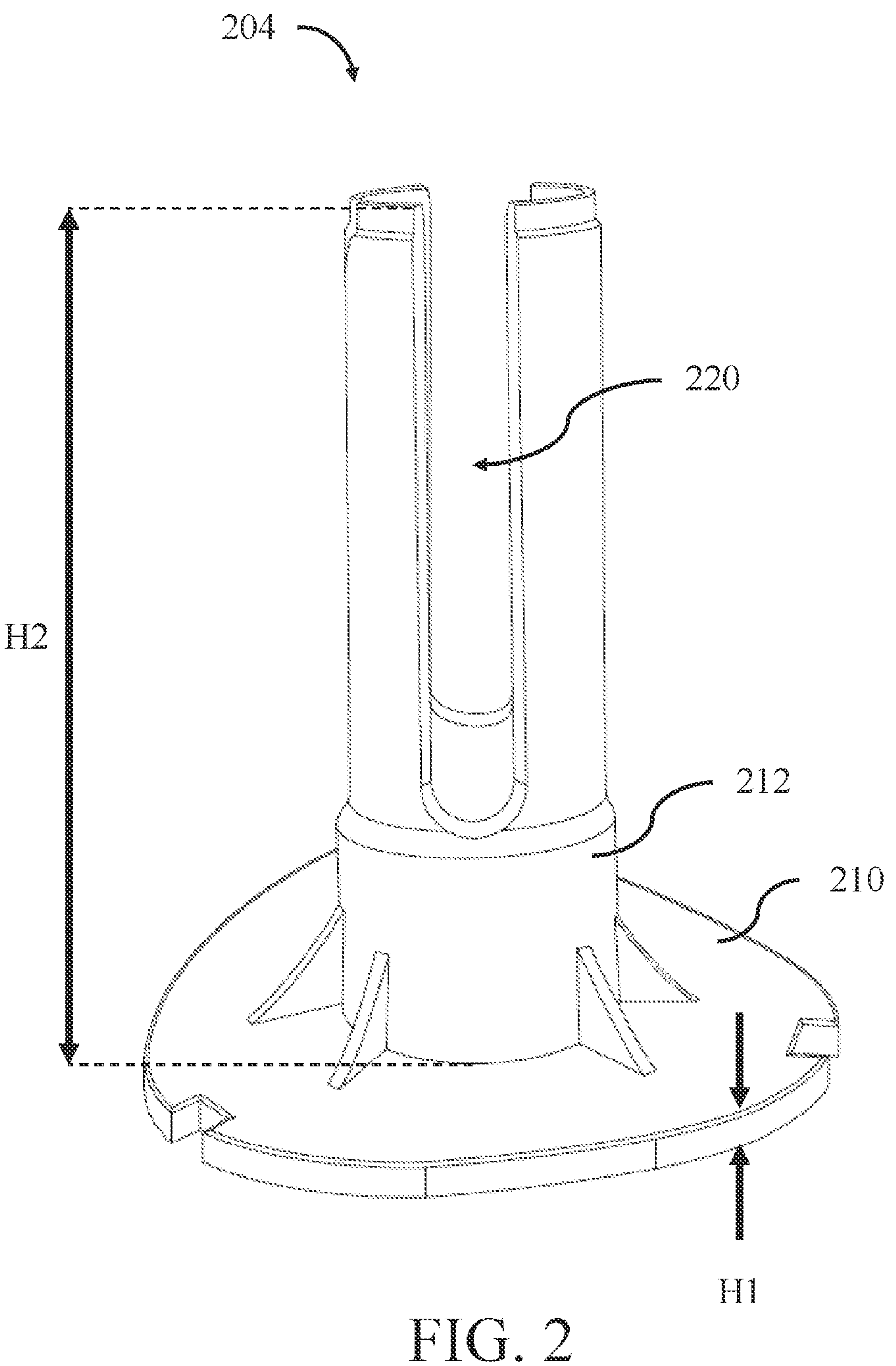
FIG. 2 is a perspective view of one embodiment of a baseplate with openings in the form of slits.
Figure 3:
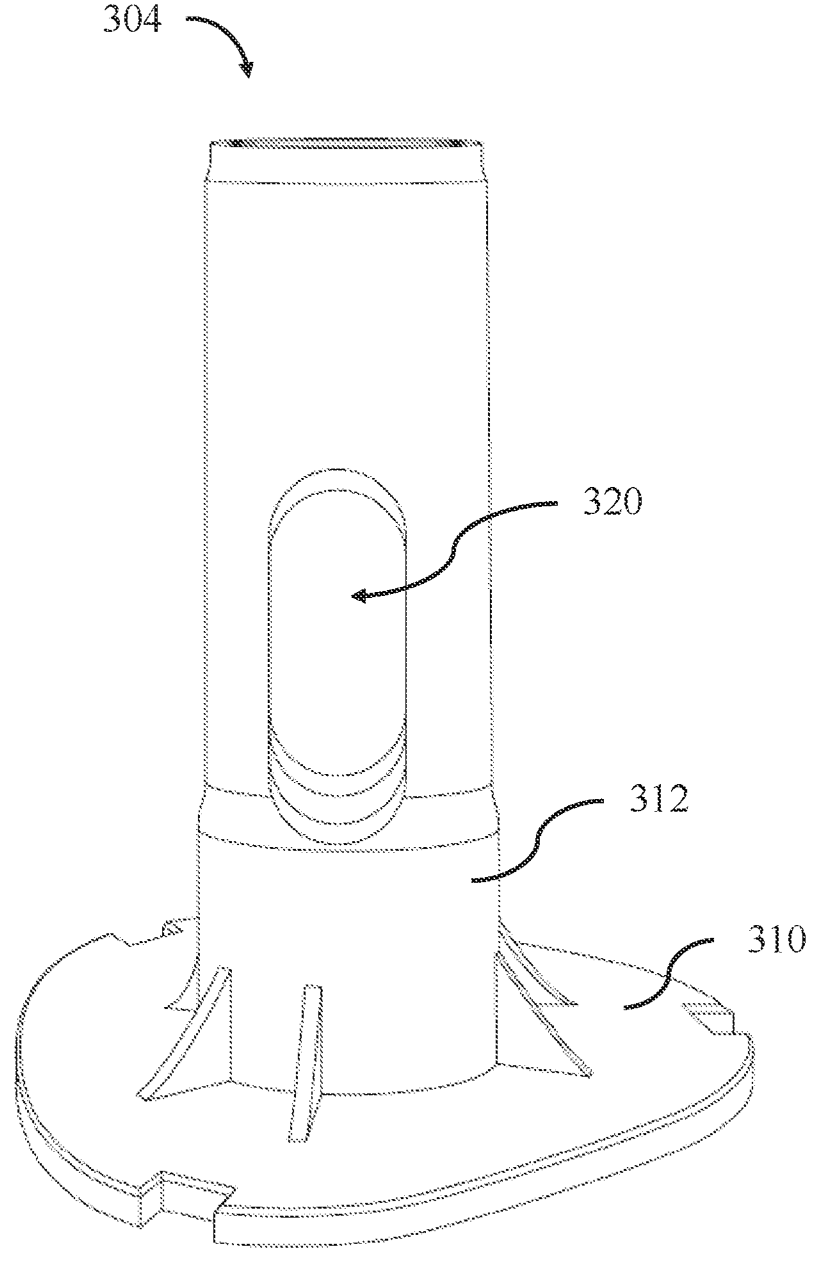
FIG. 3 is a perspective view of one embodiment of a baseplate with openings in the form of windows.
Figure 4:
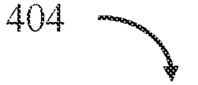
FIG. 4 is a perspective view of one embodiment of a baseplate with a short axial portion.
Figure 4:
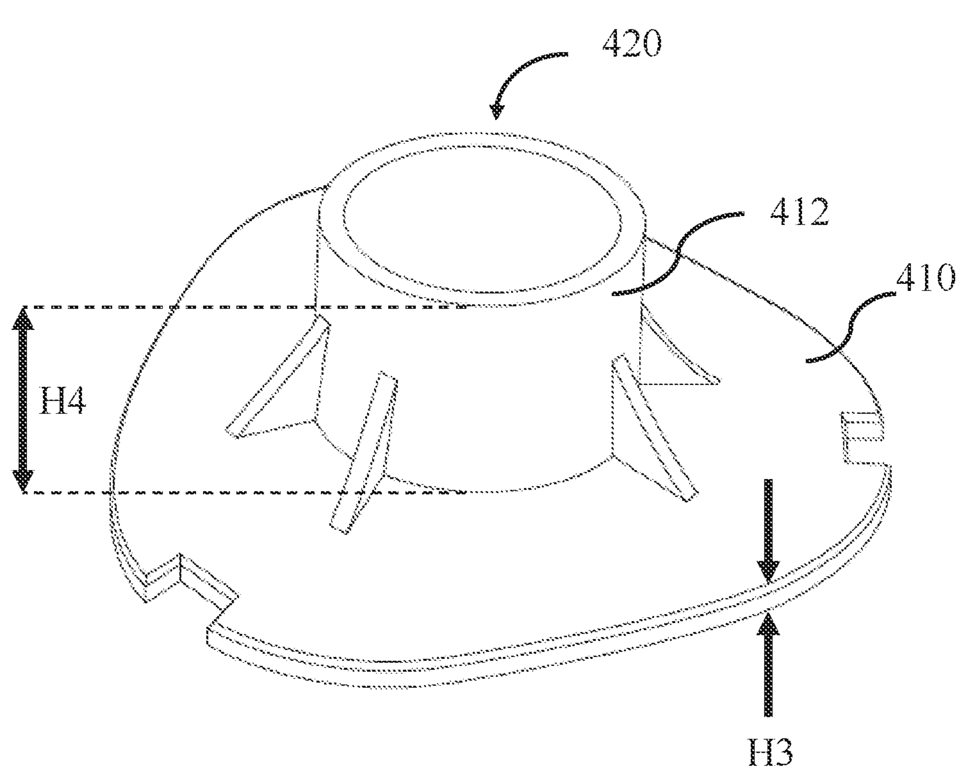

FIGS. 2-4 show different embodiments of baseplates that may be used in an injection device. FIG. 2 shows an illustrative embodiment of a baseplate 204. The baseplate 204 includes a flange portion 210 configured to contact a user's skin during injection. The baseplate 204 additionally includes an axial portion 212 in the form a tubular configuration that extends from the flange portion 210 in a longitudinal direction of a housing of an injection device. In some embodiments, an axial portion may extend substantially perpendicular to a flange portion, although other arrangements may be suitable, as the disclosure is not limited in this regard. In the embodiment of FIG. 2, the axial portion 212 of the baseplate 204 is configured to be disposed proximal a syringe in an injection device. Due in part to this arrangement, heat from a user's skin may be transferred to the flange portion 210, and from the flange portion 210 to the axial portion 212. Heat then may be transferred from the axial portion 212 to a syringe proximal the axial portion, thereby heating the syringe and subsequently heating medication within the syringe. As described above, such heat transfer may both produce a cooling effect on a user's skin and may heat medication within the syringe. The user's experience of pain and/or discomfort may be reduced by the cooling effect on the skin and/or by the heated medication.

It may be desirable to be able to view a syringe and/or medication within a syringe when a syringe is disposed within an injection device. Being able to view medication within an injection device may allow a user to identify the medication (e.g., by color, viscosity, or any other visible characteristic) to confirm that the correct medication and/or the correct state of the medication will be injected. Alternatively or in addition, a line of sight to the medication may allow a user to visually confirm that an injection has taken place (e.g., by comparing an amount of medication in a syringe before and after an injection).

However, a baseplate material with desirable characteristics (e.g., desirable heat-transfer characteristics) may be opaque or partially opaque. Using an opaque or partially opaque material for a baseplate may decrease visibility of a syringe and/or medication. With an opaque baseplate, it may be advantageous to include openings to enable a line of sight to a syringe and/or the medication within the syringe. For example, a baseplate may include one more openings such as slits, windows, voids, gaps, holes, apertures, or any other suitable feature to increase visibility.

In the embodiment of FIG. 2, the baseplate 204 includes openings defined in the axial portion 212 in the form of slits 220 that extend distally from the proximal end of the axial portion 212. Slits 220 may enable a user to view a syringe disposed within the baseplate 204. In one embodiment, a single slit is provided in the axial portion 212. In the embodiment shown, two slits are arranged circumferentially from one another in a diametric opposite relationship. More than two slits may be formed and arranged a different circumferential angles from one another.

FIG. 3 shows an alternative embodiment of a baseplate 304 having a flange portion 310 and an axial portion 312.

The baseplate 304 includes openings defined by the axial portion 310 in the form of windows 320. Windows 320 may enable a user to view a syringe disposed within an axial portion 312 of the baseplate 304. In one embodiment, a single opening is provided in the axial portion 310. In the embodiment shown, two openings are arranged circumferentially from one another in a diametric opposite relationship. More than two openings may be formed and arranged a different circumferential angles from one another.

FIG. 4 shows an alternative embodiment of a baseplate 404 in which a proximal end 420 of an axial portion 412 of the baseplate 404 is distal to at least a portion of a syringe when the syringe is in the retracted position. The limited extent of the axial portion 412 may enable a user to view a syringe disposed within the baseplate 404. The proximal extent of the axial portion 412 may coincide to be engageable with a distal end of the syringe when it is extended.

In some embodiments, a baseplate may be a material that is thermally conductive. Materials with a thermal conductivity in each of a mold flow and a mold crossflow direction of at least 24 W/(m K) may be preferred. As used herein, a thermally conductive material is configured to transfer at least 3 Watts for the initial second of the injection cycle or an average of 1.6 Watts over a period of time of 10 seconds during injection cycle from a heat source with a temperature of 37 degrees C. In some embodiments, a baseplate may be a material that is more thermally conductive than a material of the housing. In some embodiments, the baseplate may be a polymer. For example, a baseplate may be LG Chemical MABS TR558A1 or Celanese Cool Poly E3617-KD3003. Of course, other suitable polymers may be used, as the disclosure is not limited in this regard. In some embodiments, a baseplate may be an opaque, polymer material that is more thermally conductive than a material of the housing.

An axial portion of a baseplate may have any suitable height. Referring to FIG. 2, the flange portion 210 of the baseplate 204 has a thickness H1, and the axial portion 212 has a height H2. In the embodiment of FIG. 2, a ratio of the thickness of the flange portion to the height of the axial portion (i.e., the ratio H1:H2) is approximately 1:25. Referring to FIG. 4, the flange portion 410 of the baseplate 404 has a thickness H3, and the axial portion 412 has a height H4. In the embodiment of FIG. 4, a ratio of the thickness of the flange portion to the height of the axial portion (i.e., the ratio H3:H4) is approximately 1:7. In some embodiments, a ratio of a thickness of a flange portion to a height of an axial portion may be greater than or equal to 1:100, 1:50, 1:25, 1:15, 1:10, or 1:5. In some embodiments, a ratio of a thickness of a flange portion to a height of an axial portion may be less than or equal to 1:2, 1:5, 1:10, 1:15, 1:25, or 1:50. It should be appreciated that a ratio of a thickness of a flange portion to a height of an axial portion may be any suitable value, as the disclosure is not limited in this regard. The ratio H1:H2 in combination with the materials disclosed herein may provide advantages.

In some embodiments, a cross sectional area of a flange portion of a baseplate may be greater than a cross sectional area of a syringe body. In some embodiments, a cross sectional area may refer to an area in a plane perpendicular to the longitudinal axis 101 of an injection device. In some embodiments, a cross sectional area may refer to an area in a plane parallel to a plane of a distal surface of the flange portion of a baseplate. In some embodiments, a ratio of a cross sectional area of the flange portion of a baseplate to a cross sectional area of a syringe may be less than 50:1, 25:1, 10:1, or 5:1. In some embodiments, a ratio of a cross sectional area of the flange portion of a baseplate to a cross sectional area of a syringe may be greater than 2:1, 5:1, 10:1, or 25:1. It should be appreciated that a ratio of a cross sectional area of a flange portion of a baseplate to a cross sectional area of a syringe may be any suitable value, as the disclosure is not limited in this regard.

Figure 5:
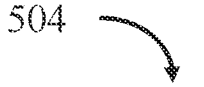
FIG. 5 is a bottom view of one embodiment of a baseplate.
Figure 5:
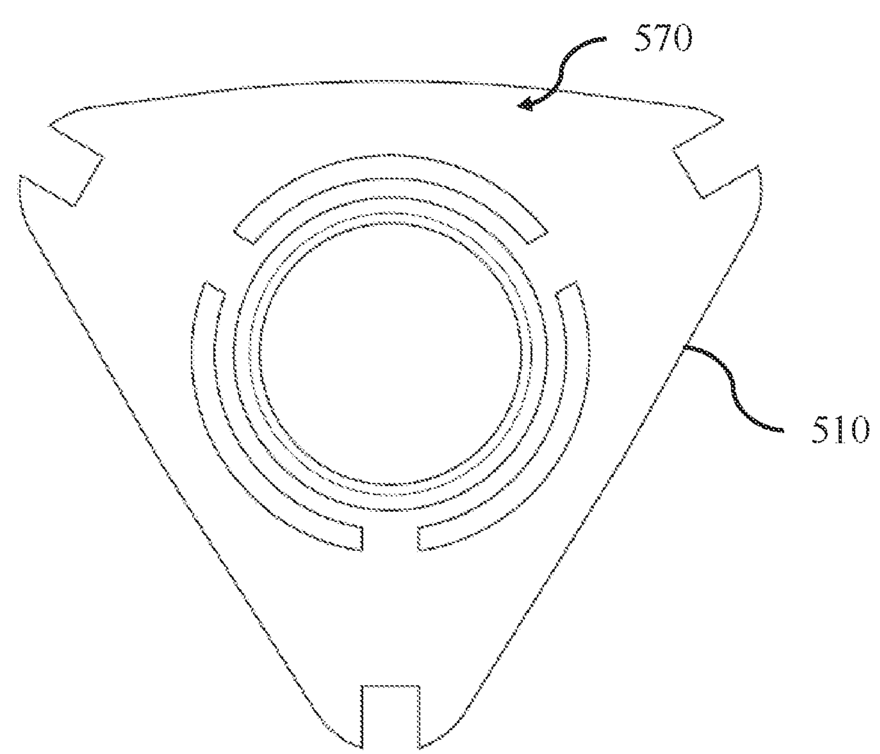
Figure 6:
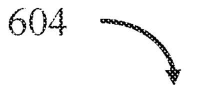
FIG. 6 is a bottom view of one embodiment of a baseplate with surface features.
Figure 6:
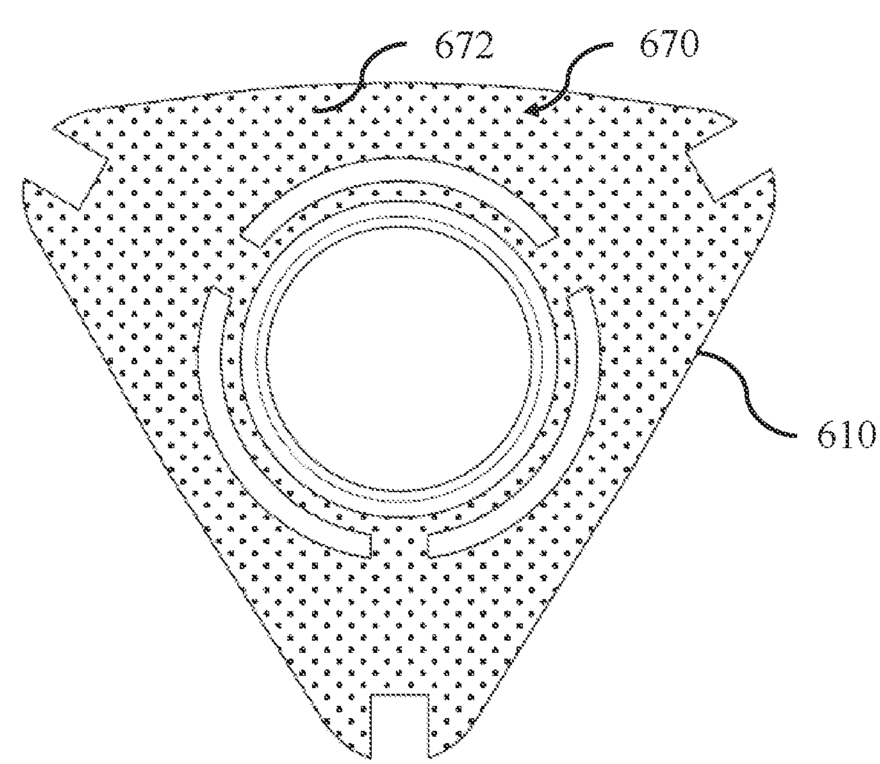

Referring now to FIGS. 5 and 6, which show bottom views of different embodiments of a baseplate, a baseplate of an injection device may include a flange portion. In the embodiment of FIG. 5, a distal surface 570 of a flange portion 510 of a baseplate 504 is smooth and untextured. In the embodiment of FIG. 6, a distal surface 670 of a flange portion 610 of a baseplate 604 is textured. The distal surface 670 includes a plurality of protrusions 672. The pattern of the protrusions may be defined to provide a desired effect. In other embodiments, other surface features may be included in addition to or in place of protrusions. Surface features may include bumps, ridges, protrusions, spikes, dimples, or any other suitable surface feature, as the disclosure is not limited in this regard. Without wishing to be bound by theory, such surface features may act as sensory disruption features which may distract a user from pain and/or discomfort during needle insertion and/or medication injection. The protrusions 672 may be formed integrally with the flange portion of the same thermally conductive material, such as the ones listed above. Alternatively, the protrusions 672 may be formed separately then attached, via mechanical attachment, adhesives, thermally fused, or the like, to the flange portion at a desired pattern. In this case, the protrusions may be still made of same thermally conductive material, such as the ones listed above, or may be made of a different material have a thermal conductivity that is greater than, less than, or equal to the thermal conductivity of the flange portion.

Figure 7:
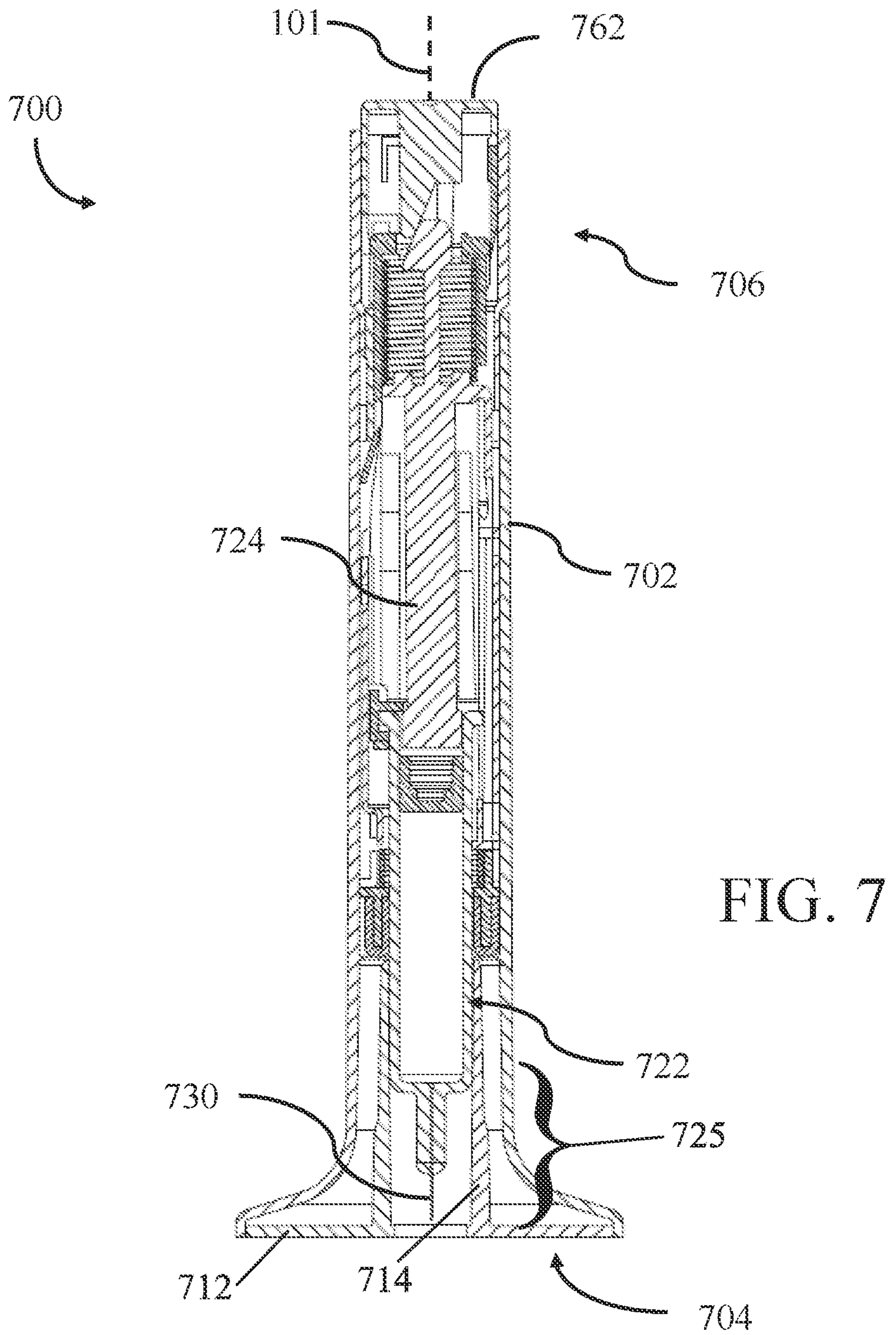
FIG. 7 is a cross sectional view of one embodiment of an injection device before deployment of a syringe.
Figure 8:
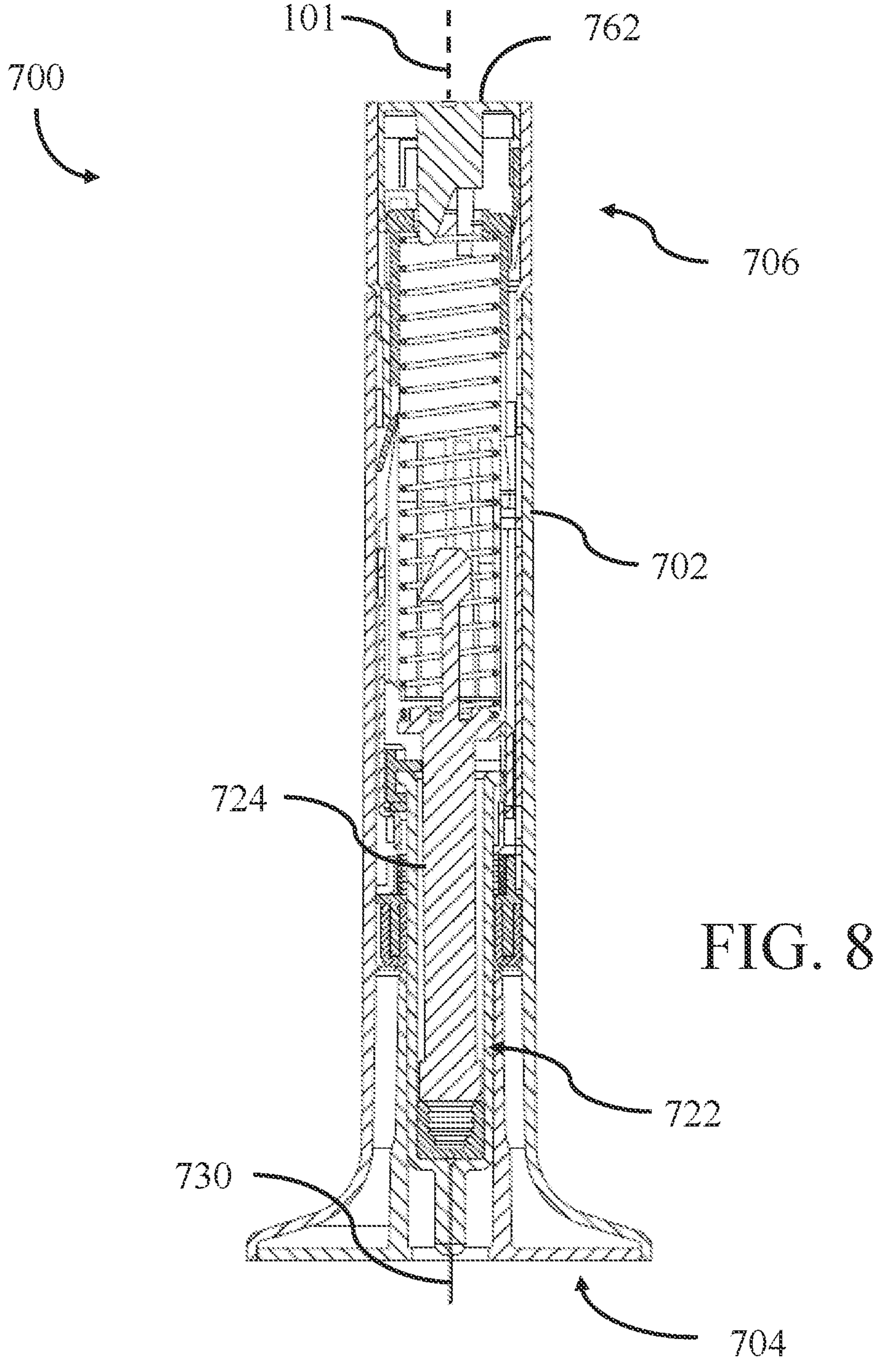
FIG. 8 is a cross sectional view of the embodiment of the injection device of FIG. 7 after deployment of the syringe and after delivery of medication.

FIGS. 7 and 8 show one embodiment of an injection device 700 in a retracted state and a deployed state, respectively. When the actuation mechanism 706 is operated, such as by depressing a button 762, the syringe 722 of the injection device 700 is automatically driven downward such that the needle 730 of the syringe 722 projects beyond the distal end of the housing 702 to penetrate the user's skin. In some embodiments, the needle 730 passes through the center of the baseplate 704 during injection. The injection device 700 then proceeds to inject the medication in the syringe through the needle by moving the plunger 724 relative to the body of the syringe 722. In some embodiments, the syringe is then retracted automatically such that the needle 730 is returned to within the housing 702. Baseplate 704 is shown inserted within the device housing 702, where the flange portion 712 forms the distal end of the device and the axial portion 714 is shown extending proximally from the flange portion 712 and in surrounding contact with the distal end of the syringe 722 when in the retracted position. A distal portion 725 of the axial portion 714 of baseplate 704 shows the axial extent to contact the syringe, which can permit heat transmission from the skin to the syringe and needle for more quickly warming the medication or fluid via the flange and axial portion.

In some embodiments, the injection device utilizes the actuation mechanisms and the injection processes described in US 2015/0246181, the entirety of which is incorporated by reference herein.

Figure 9:
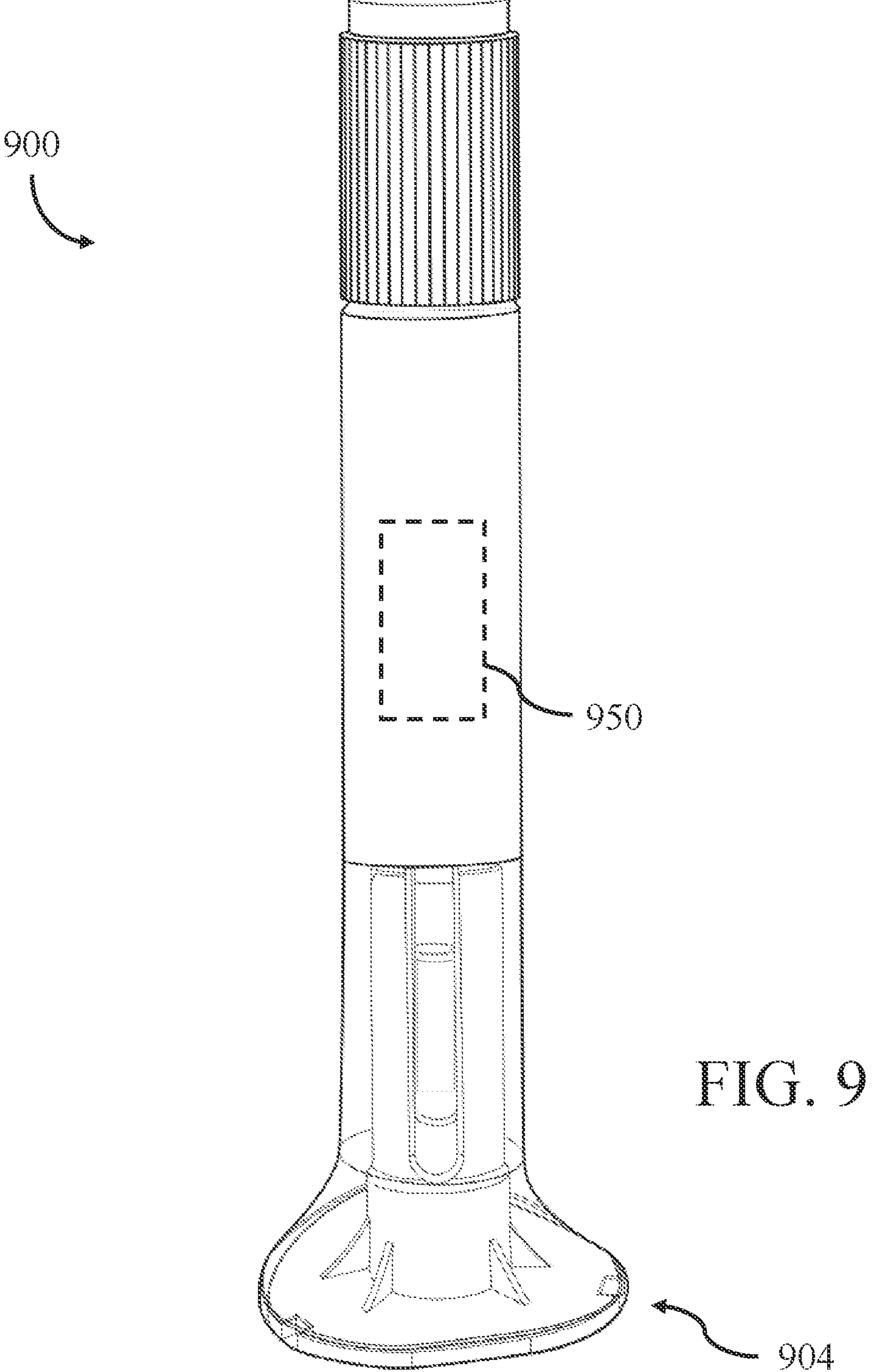
FIG. 9 is a perspective view of one embodiment of an injection device that includes a processor.

In some embodiments, an injection device may include a baseplate that is electrically conductive. An electrically conductive baseplate may be used as an antenna for broadcasting information from the injection device to an associated device. In the embodiment of FIG. 9, an injection device 900 include a processor 950. A baseplate 904 communicates via electrical wires or wirelessly with the processor 950 to enable data/information transmission either into the device or out from the device or both. The thermal conductive material listed above may also have the electrically conductive properties for the antenna to achieve both functions. In addition, the thermal conductive material listed above may also be embedded with other material having a higher electrical conductivity to enhance the broadcasting function.

In some embodiments, a baseplate of an injection device may include sensing capabilities. The baseplate 904 communicates with the processor 950 to enable sensing capabilities. For example, an injection device may identify or measure a characteristic of an injection site. Without wishing to be bound by theory, different body parts may have different characteristics. For example, fat may have a different electrical resistance than muscle. By sensing the resistivity (or the conductivity, or any other suitable parameter) of the underlying body part, an injection device may identify the body part (e.g., by determining a ratio of fat to muscle). After identifying the body part, the injection device may recommend that a user select a new injection site if the current site is determined to be undesirable. The injection device may additionally record, log, or track injection sites across multiple injections. Of course, other motivations for determining an injection site are possible, and the disclosure is not limited in this regard. The thermal conductive material listed above may also have the electrical resistive properties for the sensing to achieve both functions. In addition, the thermal conductive material listed above may also be embedded with other material having a higher electrical resistivity to enhance the sensing function. The thermal conductive material listed above may also have the electrical resistive properties and the electrical conductivity to achieve functions disclosed herein. In addition, the thermal conductive material listed above may also be embedded with other material having a higher electrical resistivity and/or higher electrical conductivity to enhance these disclosed functions.

In some embodiments, a baseplate may be used with a plurality of different injection devices. In some embodiments, an injection device may be reusable. A battery of the injection device may be able to be charged through a dock. In some embodiments, the injection device may interface with the dock through a baseplate. The baseplate may facilitate charging of the injection device. The injection device may be charged through inductive charging, conductive charging, or any suitable charging method, as the disclosure is not limited in this regard.

The above-described embodiments of the technology described herein can be implemented in any of numerous ways. For example, the embodiments may be implemented using hardware, software or a combination thereof. When implemented in software, the software code can be executed on any suitable processor or collection of processors, whether provided in a single computing device or distributed among multiple computing devices. Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semicustom circuitry resulting from configuring a programmable logic device. As yet a further alternative, a processor may be a portion of a larger circuit or semiconductor device, whether commercially available, semi-custom or custom. As a specific example, some commercially available microprocessors have multiple cores such that one or a subset of those cores may constitute a processor. Though, a processor may be implemented using circuitry in any suitable format.

Further, it should be appreciated that a computing device may be embodied in any of a number of forms, such as a rack-mounted computer, a desktop computer, a laptop computer, or a tablet computer. Additionally, a computing device may be embedded in a device not generally regarded as a computing device but with suitable processing capabilities, including a Personal Digital Assistant (PDA), a smart phone, tablet, or any other suitable portable or fixed electronic device.

Also, a computing device may have one or more input and output devices. These devices can be used, among other things, to present a user interface. Examples of output devices that can be used to provide a user interface include display screens for visual presentation of output and speakers or other sound generating devices for audible presentation of output. Examples of input devices that can be used for a user interface include keyboards, individual buttons, and pointing devices, such as mice, touch pads, and digitizing tablets. As another example, a computing device may receive input information through speech recognition or in other audible format.

Such computing devices may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the embodiments described herein may be embodied as a computer readable storage medium (or multiple computer readable media) (e.g., a computer memory, one or more floppy discs, compact discs (CD), optical discs, digital video disks (DVD), magnetic tapes, flash memories, RAM, ROM, EEPROM, circuit configurations in Field Programmable Gate Arrays or other semiconductor devices, or other tangible computer storage medium) encoded with one or more programs that, when executed on one or more computers or other processors, perform methods that implement the various embodiments discussed above. As is apparent from the foregoing examples, a computer readable storage medium may retain information for a sufficient time to provide computer-executable instructions in a non-transitory form. Such a computer readable storage medium or media can be transportable, such that the program or programs stored thereon can be loaded onto one or more different computing devices or other processors to implement various aspects of the present disclosure as discussed above. As used herein, the term "computer-readable storage medium" encompasses only a non-transitory computer-readable medium that can be considered to be a manufacture (i.e., article of manufacture) or a machine. Alternatively or additionally, the disclosure may be embodied as a computer readable medium other than a computer-readable storage medium, such as a propagating signal.

The terms "program" or "software" are used herein in a generic sense to refer to any type of computer code or set of computer-executable instructions that can be employed to program a computing device or other processor to implement various aspects of the present disclosure as discussed above. Additionally, it should be appreciated that according to one aspect of this embodiment, one or more computer programs that when executed perform methods of the present disclosure need not reside on a single computing device or processor, but may be distributed in a modular fashion amongst a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

EXAMPLES

The following Examples have been included to illustrate modes of the presently disclosed subject matter. In light of the present disclosure and the general level of skill in the art, those of skill will appreciate that the following Examples are intended to be exemplary only and that numerous changes, modifications, and alterations can be employed without departing from the scope of the presently disclosed subject matter.

Disclosed herein are methods and systems for providing "enhanced cooling" to improve VAS pain scores with a device where thermal transfer of heat away from patient's skin through a portion of the device is based on simulations relying on computational fluid dynamics (CFD) techniques. The methods and systems were successfully tested for thermal transfer via the device against a patient, using a validated computer simulation model including consideration of materials, device component construction, and an initial temperature of device.

Example 1

Figure 10B:
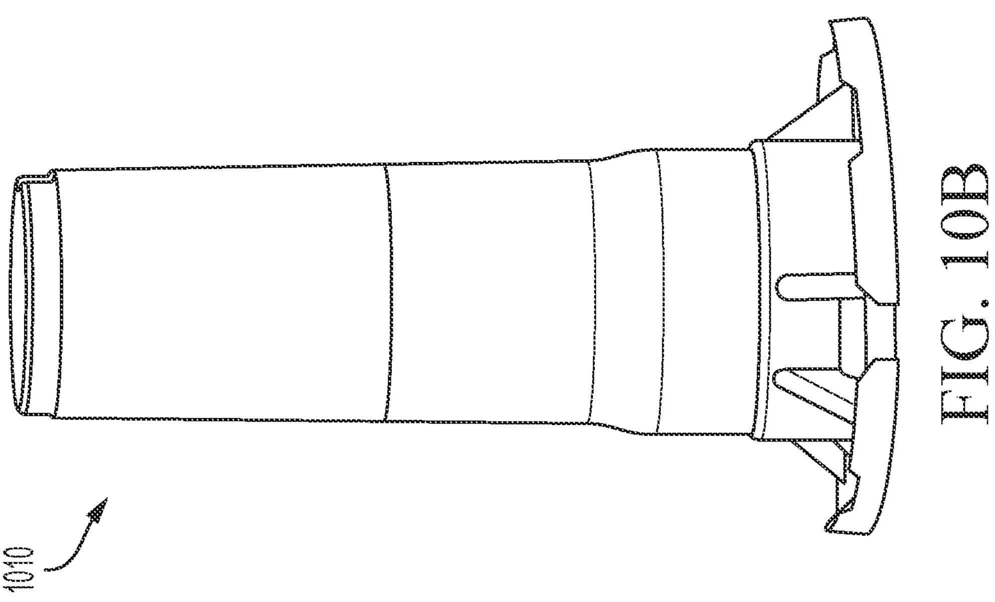
FIG. 10B is a perspective view of a baseplate made of a material different than the first material.
Figure 10A:
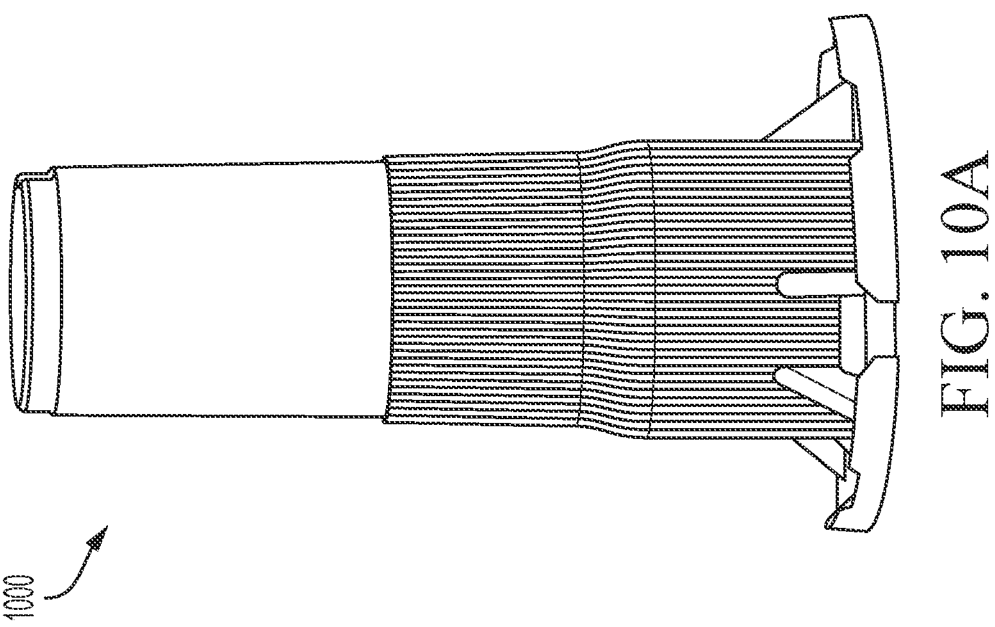
FIG. 10A is a perspective view of a baseplate made of a first material.

Model Injection Device with Initial Temperature of 25 Degrees C. Utilizing Different Materials The results of the CFD simulations described herein illustrate the importance of materials with thermal conductivity each of a mold flow and a mold crossflow of at least 24 W/(m K) and above. Starting with the concept of an injection device with a relatively wider base, that is the radius of the base is greater than the elongate body, it has been combined with the advantages offered by thermal conductive materials as disclosed herein in order to reduce the perception of pain by a patient. FIGS. 10A-10B illustrate the concept of the design, showing the device baseplates 1000, 1010, respectively. The baseplate simulated is similar to the design in FIGS. 2 and 3, but without the slot or window opening. The baseplate 1000 and the baseplate 1010 have the essentially the same geometry, except the baseplate 1000 includes a region of surface features. The baseplates are made of moldable polymer materials having different rates of heat transmissivity properties (in W/(m K)), oriented along mold flows (flow direction) and across mold flows (crossflow direction).

Baseplate 1000 is made from a first material, such as, for example, Methyl Methacrylate/ABS (MABS) TR558A provided by LG Chemical Ltd., having the following characteristics under ASTM E 1461 standard: thermal conductivity, flow of 0.25 W/(m K); and thermal conductivity, crossflow of 0.25 W/(m K). The first material may also be characterized as isotropic, where the thermal conductivity in the flow is substantially equal to the crossflow, or in another way, the ratio of thermal conductivity, flow/thermal conductivity, crossflow is substantially equal to 1. Baseplate 1000 of the first material has a density of 1050 kg/cubic meters and a weight of approximately 3 grams.

Baseplate 1010 is made from a second material, such as, for example, COOLPOLY® E3617 provided by Celanese Corporation, having the following characteristics under ASTM E 1461 standard: thermal conductivity, flow of 31 W/(m K); and thermal conductivity, crossflow of 24 W/(m K). The second material may also be characterized as anisotropic, where the thermal conductivity in the flow is greater than the crossflow, or in another way, the ratio of thermal conductivity, flow/thermal conductivity, crossflow is greater than 1, in this case 1.29. Baseplate 1010 of the second material has a density of 1620 kg/cubic meters and a weight of approximately 4.5 grams.

For the purpose of structural simulation, a finite element formulation of this model has been developed and successfully implemented into the commercial finite element code ANSYS (Seelecke & Papenfuss, 2000, Frautschi & Seelecke, 2003).

To guide the design process, a series of finite element simulations can be performed. ANSYS can be used as a platform, which allows for geometry import from the 3D solid modeling program used for the device with the improved baseplate design. The device with baseplate of different materials can be modeled by appropriate shell elements, with the FE implementation of a version of the Mueller-Achenbach model can be used. This combination allows for a realistic determination of the time-dependent thermal transmission together with the necessary forces and related starting temperature.

For the purpose of the simulated test, the device with the baseplate of the materials, oriented vertically in the direction of gravity, above was placed against a plate, oriented orthogonal to the device, simulating skin properties of a patient having a temperature of 37 degrees C., in a box with six open sides defining an ambient air environment with a temperature of 25 degrees C., that is room temperature. A clock timer was started when the device is placed against the plate skin. The thermal transmission of the heat from the plate skin throughout the baseplate was modeled dynamically for a time of 10 second, including tracking temperature and power transferred from skin plate to the baseplate.

Figures 11A, 11B:
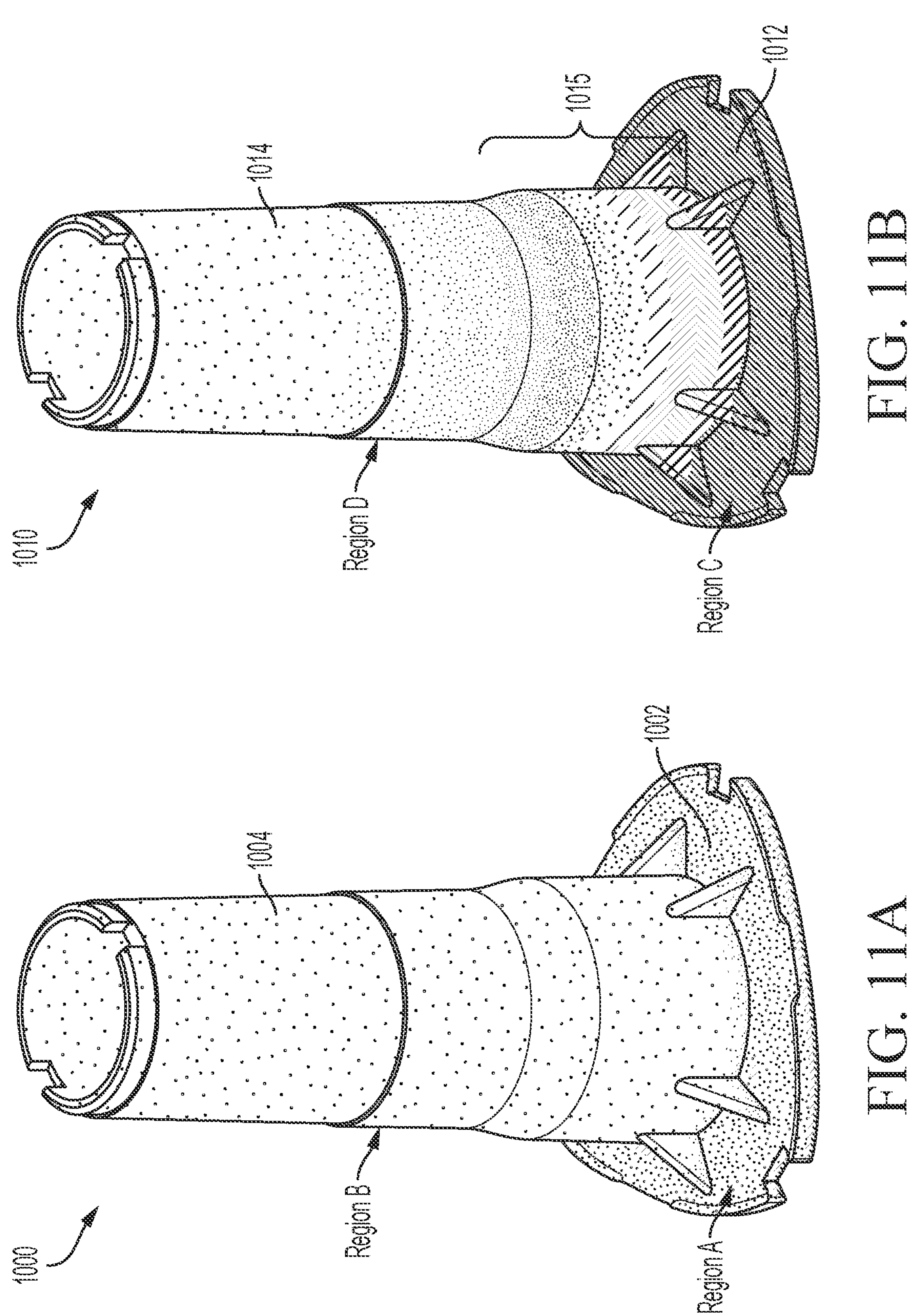
FIG. 11A show a heat transfer mapping of the baseplate in FIG. 10A after a simulated test for a period of time.
FIG. 11B show a heat transfer mapping of the baseplate in FIG. 10B after a simulated test for a period of time.

For the first simulated test, the device has an initial temperature of 25 degrees C. FIGS. 11A and 11B show heat transfer mapping of the baseplates 1000, 1010, respectively, after the simulated test of 10 seconds. Baseplate 1000 is illustrated with two regions of heating. One region A is associated with the flange portion 1002 of the baseplate 1000, indicating a temperature ranging from 30 degrees C. to 37 degrees C. Second region B is associated with the entire axial portion 1004 of the baseplate 1000, indicating no temperature rise, that is, a temperature of 25 degrees C. Baseplate 1010 is illustrated with multiple regions of heating. The entire flange portion 1012 of the baseplate 1010, shown at region C, for indicating a temperature 37 degrees C. Second region C is associated with the axial portion 1014 of the baseplate 1010, indicating a temperature range of 25 degrees C. to 37 degrees C. More specifically, the distal portion of the axial portion 1014 of baseplate 1010, shown as ref num. 1015, that is associated with surrounding and in contact with the syringe when in the retracted position, is shown as rising in temperature due to heat transmitted from the plate skin, ranging in temperature from 30 degrees C. to 37 degrees C., or a rise in temperature of 5 to 7 degrees C.

Figure 12:
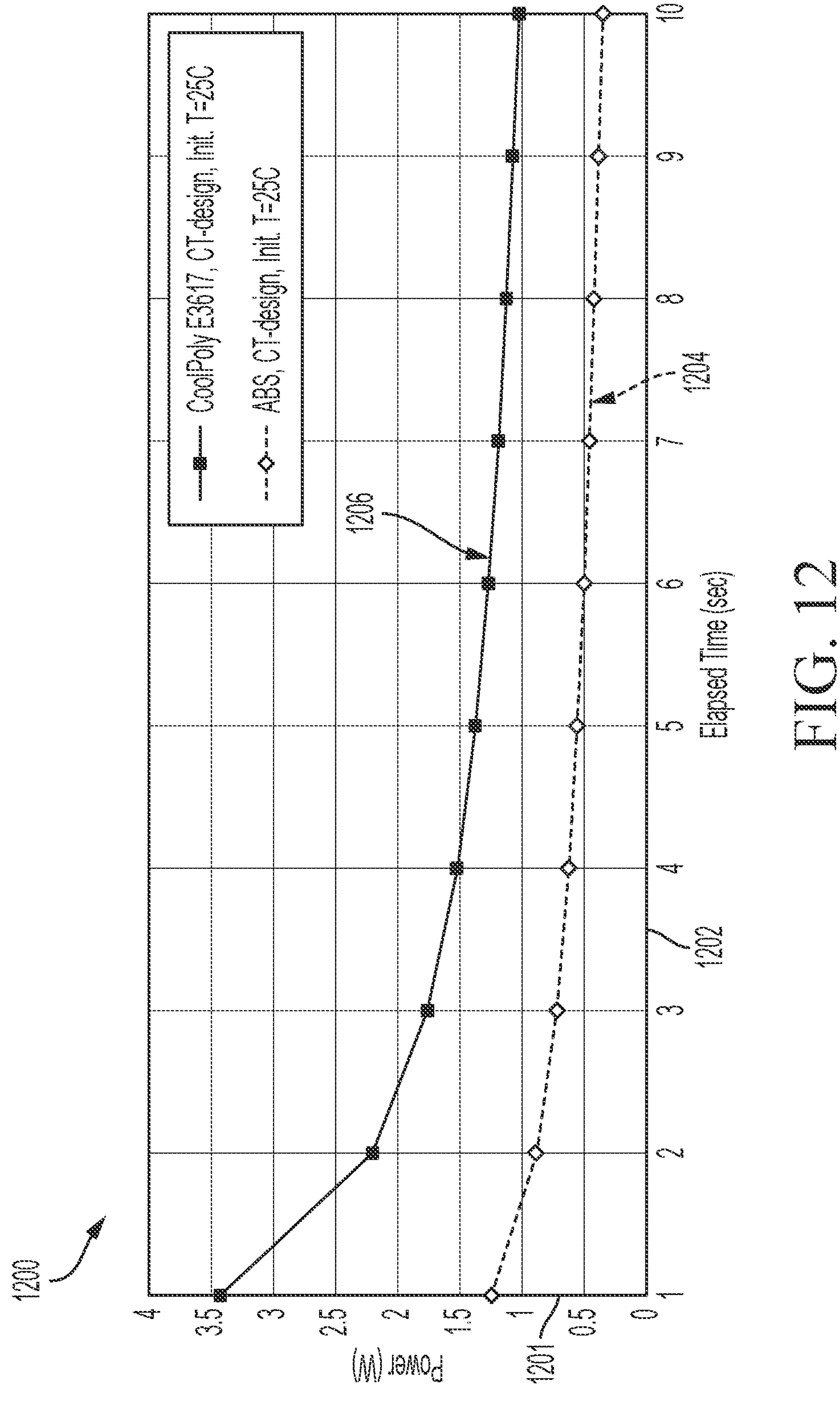
FIG. 12 is a graph of power (Watts) (y-axis) transferred from the baseplates of FIGS. 10A-10B over a period of time (seconds) (x-axis) from the simulated test.

FIG. 12 is a graph 1200 of the power in Watts (1201) (y-axis) transferred from the skin plate to the baseplate of the device having an initial temperature of 25 degrees C. over a period of time (1202) (x-axis) for ten seconds from the first simulated test. A first line 1204 indicates the power transferred of the device with the first material. A second line 1206 indicates the power transferred of the device with the second material. The average power (W) of the device with the first material over the ten seconds was 0.6 W. The average power (W) of the device with the second material over the ten seconds was 1.6 W. It is surprising that the initial power at time (1 sec) is markedly better with the device with the second material. The power (W) of the device with the first material at time of 1 second was 1.25 W, while the power (W) of the device with the second material at time of 1 second was 3.5 W. This degree of power transfer at the initial start of injection contributes to the instant cooling the patient feels during the injection, as well as the temperature rise of the baseplate and transfer of this heat to the syringe and needle. Baseplate comprises a material configured to transfer at least 3 Watts for the initial second or an average of 1.6 Watts over a period of time of 10 seconds from a heat source with a temperature of 37 degrees C.

Example 2

Model Injection Device with Initial Temperature of 5 Degrees C. Utilizing Different Materials For the second simulated test, the device has an initial temperature of 5 degrees C. to indicate that device was pre-chilled prior to use, while everything else remained the same as discussed above with Example 1. The power in Watts was transferred from the skin plate to the baseplate of the device having an initial temperature of 5 degrees C. over a period of time of ten seconds. The average power (W) of the device with the first material over the ten seconds was 1.6 W. The average power (W) of the device with the second material over the ten seconds was 4.2 W, almost 2.5 times greater than the first material. The power transfer at the initial start of injection contributes to the instant cooling the patient feels during the injection, as well as the temperature rise of the baseplate and transfer of this heat to the syringe and needle.

Figure 13:
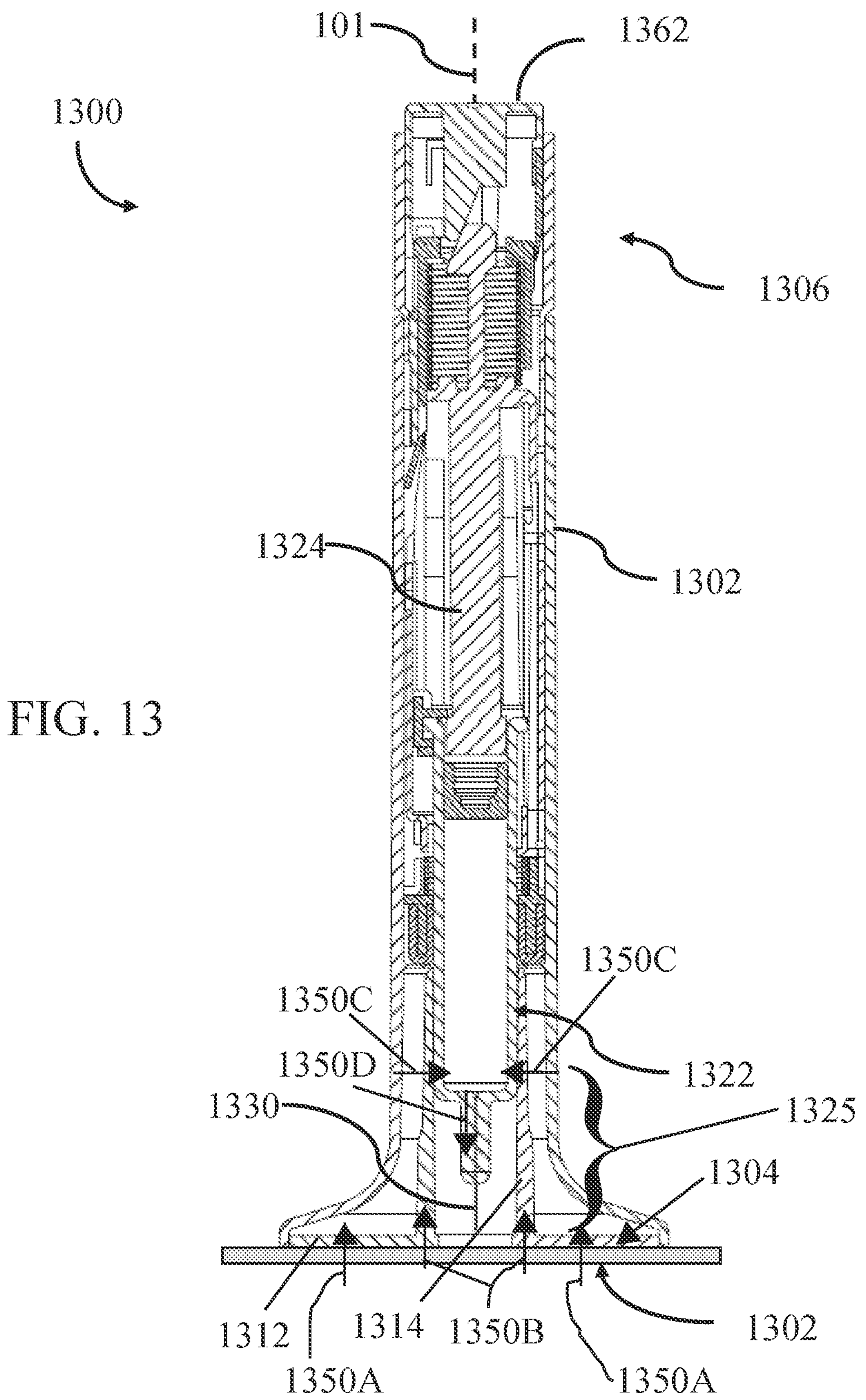
FIG. 13 illustrates a heat path of an injection device placed against a skin of a patient, depicting heat being transmitted directly to a needle of the injection device from the skin.

FIG. 13 illustrates the heat path in one embodiment of an injection device 1300 in a retracted state placed against the skin 1302 of a patient. When the actuation mechanism 1306 is operated, such as by depressing a button 1362, the syringe 1322 of the injection device 1300 is automatically driven downward such that the needle 1330 of the syringe 1322 projects beyond the distal end of the housing 1302 to penetrate the user's skin 1302. In some embodiments, the needle 1330 passes through the center of the baseplate 1304 during injection. The injection device 1300 then proceeds to inject the medication in the syringe through the needle by moving the plunger 1324 relative to the body of the syringe 1322. In some embodiments, the syringe is then retracted automatically such that the needle 1330 is returned to within the housing 1302, such as shown in FIG. 8. Baseplate 1304 is shown inserted within the device housing 1302, where the flange portion 1312 forms the distal end of the device and the axial portion 1314 is shown extending proximally from the flange portion 1312 and in surrounding contact with the distal end of the syringe 1322 when in the retracted position. A distal portion 1325 of the axial portion 1314 of baseplate 1304 shows the axial extent to contact the syringe 1322, which can permit heat transmission from the skin to the syringe 1322 and needle 1330 for more quickly warming the medication or fluid via the flange and axial portions, 1312, 1314. The following arrows are used to illustrate the heat transmission from the skin to the needle. Arrows 1350A depict heat being transmitted directly to the flange portion 1312 from the skin 1302 from being in direct contact therewith. Arrows 1350B depict heat being transmitted directly to the flange portion 1312, in addition to the axial portion 1314, from the skin 1302 from being in direct contact therewith. Arrows 1350C depict heat being transmitted directly to the syringe 1322 from the axial portion 1314 and distal portion 1325 from the source of the skin. Arrow 1350D depicts heat being transmitted directly to the needle 1330 from the syringe 1322 from the source of the skin.

One of the advantages of an injection device with a thermal conductive baseplate described herein is the ability to more quickly wick heat away from the patient's body for providing the feeling of localized cooling for the injection. The localized cooling may reduce the perception of pain felt by the patient during the injection. This heat that is wicked away can be transmitted to the syringe to warm the medication in the syringe, such medication may be room temperature or chilled during storage prior to use, and in the needle during the injection as heat is transmitted from the syringe to the needle. Such thermally conductive material can be molded into the configuration shown the in the figures to aid in more efficient manufacturing for high volume manufacturing setting. In some embodiment, the baseplate may be made of a material embedded with thermal fibers or flecks to enhance thermal transmission. In other embodiments, the flange portion may be made of a different material than the axial portion, each material contributing to the thermal transmission.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed.

While various embodiments have been described, it will be apparent to those of ordinary skill in the art that many more embodiments and implementations are possible. Accordingly, the embodiments described herein are examples, not the only possible embodiments and implementations. Furthermore, the advantages described above are not necessarily the only advantages, and it is not necessarily expected that all of the described advantages will be achieved with every embodiment.

Various aspects are described in this disclosure, which include, but are not limited to, the following aspects:

1. An injection device comprising: a housing; a baseplate coupled to the housing, the baseplate including a flange portion and an axial portion that extends from the flange portion in a longitudinal direction of the housing, wherein the baseplate is an opaque, polymer material that is more thermally conductive than a material of the housing; a syringe at least partially disposed within the housing, the syringe including a needle; and a deployment mechanism configured to move the syringe relative to the housing from a retracted position to a deployed position in which the needle projects beyond the baseplate, wherein at least a portion of the syringe is visible when the syringe is in the retracted position.

2. An injection device comprising: a housing; a thermally conductive baseplate coupled to the housing, the baseplate including a flange portion and an axial portion that extends from the flange portion in a longitudinal direction of the housing, wherein the axial portion includes an opening passing through the axial portion in a direction perpendicular to the longitudinal direction; and a deployment mechanism configured to move a syringe relative to the housing from a retracted position to a deployed position in which a needle of the syringe projects beyond the baseplate.

3. The injection device of any one of aspects 1-2, wherein the axial portion of the baseplate includes an opening passing through the axial portion in a direction perpendicular to the longitudinal direction, and the at least a portion of the syringe is visible through the opening.

4. The injection device of any one of aspects 1-3, wherein a proximal end of the axial portion of the baseplate is distal to a proximal end of the syringe when the syringe is in the retracted position.

5. The injection device of any one of aspects 1-4, wherein the baseplate is electrically conductive or resistive.

6. The injection device of any one of aspects 1-5, wherein the opening includes one or more selected from the group of a slit, a gap, a window, a hole, and an aperture.

7. The injection device of any one of aspects 1-6, wherein the baseplate comprises a material configured to transfer at least 3 Watts for the initial second of injection or an average of 1.6 Watts over a period of time of 10 seconds from a heat source with a temperature of 37 degrees C.

8. The injection device of any one of aspects 1-7, wherein the baseplate comprises a material with a thermal conductivity in each of a mold flow and a mold crossflow directions of at least 24 W/(m K).

9. The injection device of any one of aspects 1-8, wherein a skin-contacting surface of the flange portion of the baseplate includes a plurality of protrusions.

10. The injection device of any one of aspects 1-9, wherein the syringe is filled with a medication.

11. The injection device of aspect 10, wherein at least a portion of the medication is visible when the syringe is in the retracted position.

12. A method of transferring heat to a syringe, the method comprising: bringing a baseplate of an injection device into contact with a user's skin; transferring heat from the user's skin to the baseplate; and transferring heat from the baseplate to a syringe proximate the baseplate.

13. The method of aspect 12, further comprising heating medication within the syringe.

14. The method of aspect any one of aspects 12-13, wherein bringing the baseplate of the injection device into contact with the user's skin includes bringing a surface of a flange portion of the baseplate of the injection device into contact with the user's skin.

15. The method of any one of aspects 12-14, wherein transferring heat from the baseplate to the syringe includes transferring heat from a surface of an axial portion of the baseplate to the syringe.

16. The method of any one of aspects 12-15, further comprising conducting heat along at least a portion of the baseplate prior to transferring heat from the baseplate to the syringe.

17. The method of aspect 16, wherein conducting heat along the at least a portion of the baseplate includes conducting heat along an axial portion of the baseplate.

18. The method of any one of aspects 12-17, wherein at least one of wherein the baseplate comprises a material configured to transfer at least 3 Watts for the initial second of injection or an average of 1.6 Watts over a period of time of 10 seconds from a heat source with a temperature of 37 degrees C. and wherein the baseplate comprises a material with a thermal conductivity in each of a mold flow and a mold crossflow directions of at least 24 W/(m K).

What is claimed is:

1. An injection device comprising:

a housing;

a baseplate coupled to the housing, the baseplate including a flange portion and an axial portion that extends from the flange portion in a longitudinal direction of the housing, wherein the baseplate is an opaque, polymer material that is more thermally conductive than a material of the housing; and a syringe at least partially disposed within the housing, the syringe including a needle, wherein the syringe is movable relative to the housing from a retracted position to a deployed position in which the needle projects beyond the baseplate, wherein at least a portion of the syringe is visible when the syringe is in the retracted position, wherein the baseplate comprises a material configured to transfer at least 3 Watts for the initial second of injection or an average of 1.6 Watts over a period of time of 10 seconds from a heat source with a temperature of 37 degrees C.

2. The injection device of claim 1, wherein the syringe is filled with a medication.

3. The injection device of claim 2, wherein at least a portion of the medication is visible when the syringe is in the retracted position.

4. The injection device of claim 1, wherein the axial portion of the baseplate includes an opening passing through the axial portion in a direction perpendicular to the longitudinal direction, and the at least a portion of the syringe is visible through the opening.

5. The injection device of claim 4, wherein the opening includes one or more selected from the group of a slit, a gap, a window, a hole, and an aperture.

6. The injection device of claim 1, wherein a proximal end of the axial portion of the baseplate is distal to a proximal end of the syringe when the syringe is in the retracted position.

7. The injection device of claim 1, wherein a skin-contacting surface of the flange portion of the baseplate includes a plurality of protrusions.

8. The injection device of claim 1, wherein the baseplate is electrically conductive or/and resistive.

9. An injection device comprising:

a housing;

a thermally conductive baseplate coupled to the housing, the baseplate including a flange portion and an axial portion that extends from the flange portion in a longitudinal direction of the housing, wherein the axial portion includes an opening passing through the axial portion in a direction perpendicular to the longitudinal direction; and a syringe movable relative to the housing from a retracted position to a deployed position in which a needle of the syringe projects beyond the baseplate, wherein the baseplate comprises a material with a thermal conductivity in each of a mold flow and a mold crossflow directions of at least 24 W/(m K).

10. The injection device of claim 9, wherein at least a portion of the syringe is visible through the opening.

11. The injection device of claim 9, wherein the opening includes one or more selected from the group of a slit, a gap, a window, a hole, and an aperture.

12. The injection device of claim 9, wherein the syringe is filled with a medication, and wherein at least a portion of the medication is visible when the syringe is in the retracted position.

13. The injection device of claim 9, wherein a skin-contacting surface of the flange portion of the baseplate includes a plurality of protrusions.

14. The injection device of claim 9, wherein the material of the baseplate has electrically conductive or/and resistive properties.

15. An injection device comprising:

a housing;

a baseplate coupled to the housing, the baseplate including a flange portion and an axial portion that extends from the flange portion in a longitudinal direction of the housing, wherein the baseplate comprises a thermal conductive material that is more thermally conductive than a material of the housing;

a reservoir at least partially disposed within the housing, a needle coupled to the reservoir; and the needle is moved to project beyond the baseplate, wherein the axial portion of the baseplate is in contact with the reservoir, and wherein in response to skin contact with the flange portion, heat is configured to be transmitted through the flange portion and the axial portion of the baseplate and to the reservoir.

16. The injection device of claim 15, wherein a surface of the flange portion to be in contact with the syringe includes a plurality of protrusions.

17. The injection device of claim 15, wherein the thermal conductive material of the baseplate is configured to wick away heat from the skin at a power (W) of 3.5 W within a first second of skin contact.

18. The injection device of claim 15, wherein the thermal conductive material of the baseplate has electrically conductive or/and resistive properties.

* * * * *